US00PP24336P2

(12) United States Plant Patent
Woods

(10) Patent No.: US PP24,336 P2
(45) Date of Patent: Mar. 25, 2014

(54) ***HIBISCUS* PLANT NAMED 'JWNWOOD 4'**

(50) Latin Name: *Hibiscus syriacus*
Varietal Denomination: JWNWOOD 4

(75) Inventor: Roderick Woods, Runcton Holme (GB)

(73) Assignee: John Woods Nurseries, Runcton Home, Norfolk (GB)

( * ) Notice: Subject to any disclaimer, the term of this patent is extended or adjusted under 35 U.S.C. 154(b) by 139 days.

(21) Appl. No.: 13/506,083

(22) Filed: Mar. 24, 2012

(51) Int. Cl.
*A01H 5/00* (2006.01)

(52) U.S. Cl.
USPC ..... Plt./257

(58) Field of Classification Search
USPC ..... Plt./257
See application file for complete search history.

(56) References Cited

U.S. PATENT DOCUMENTS

PP12,612 P2 * 5/2002 Woods ..... Plt./257
PP20,574 P2 * 12/2009 Woods ..... Plt./257
PP20,579 P2 * 12/2009 Gerlt ..... Plt./257

OTHER PUBLICATIONS

UPOV PLUTO QZ Citation for 'JWNWOOD4' Jun. 15, 2012.*
UPOV PLUTO CA Citation for 'JWNWOOD4' Oct. 31, 2011.*

* cited by examiner

*Primary Examiner* — Wendy C Haas
(74) *Attorney, Agent, or Firm* — C. A. Whealy

(57) ABSTRACT

A new and distinct cultivar of *Hibiscus* plant named 'JWNWOOD 4', characterized by its upright and outwardly spreading plant habit; vigorous growth habit; freely branching habit; large light pink-colored flowers with numerous petaloids; and good garden performance.

2 Drawing Sheets

Botanical designation: *Hibiscus syriacus*.
Cultivar denomination: 'JWNWOOD 4'.

BACKGROUND OF THE INVENTION

The present invention relates to a new and distinct cultivar of *Hibiscus*, botanically known as *Hibiscus syriacus*, commercially known as Rose-of-Sharon or Althea, and hereinafter referred to by the name 'JWNWOOD 4'.

The new *Hibiscus* plant is a product of a planned breeding program conducted by the Inventor in Runcton Holme, Norfolk, United Kingdom. The objective of the breeding program was to develop new *Hibiscus* plants with large pink-colored flowers.

The new *Hibiscus* plant originated from a cross-pollination conducted by the Inventor in July, 2003 of a proprietary selection of *Hibiscus syriacus* identified as code number 3311, not patented, as the female, or seed, parent with a proprietary selection of *Hibiscus syriacus* identified as code number 4243, not patented, as the male, or pollen, parent. The new *Hibiscus* plant was discovered and selected by the Inventor on Sep. 4, 2006 as a single flowering plant within the progeny of the stated cross-pollination in a controlled outdoor nursery environment in Runction Holme, Norfolk, United Kingdom.

Asexual reproduction of the new *Hibiscus* plant by softwood cuttings in a controlled greenhouse environment in Runcton Holme, Norfolk, United Kingdom has shown that the unique features of this new *Hibiscus* plant are stable and reproduced true to type in successive generations of asexual reproduction.

SUMMARY OF THE INVENTION

Plants of the new *Hibiscus* have not been observed under all possible environmental conditions and cultural practices.

The phenotype may vary somewhat with variations in environmental conditions such as temperature and light intensity without, however, any variance in genotype.

The following traits have been repeatedly observed and are determined to be the unique characteristics of 'JWNWOOD 4'. These characteristics in combination distinguish 'JWNWOOD 4' as a new and distinct *Hibiscus* plant:

1. Upright and outwardly spreading plant habit.
2. Vigorous growth habit.
3. Freely branching habit.
4. Large light pink-colored flowers with numerous petaloids.
5. Good garden performance.

Plants of the new *Hibiscus* can be compared to plants of the female parent selection. Plants of the new *Hibiscus* differ primarily from plants of the female parent selection in flower color and flower form as plants of the female parent selection have white-colored flowers with fewer petaloids.

Plants of the new *Hibiscus* can be compared to plants of the male parent selection. Plants of the new *Hibiscus* differ primarily from plants of the male parent selection in flower color and flower form as plants of the male parent selection have white-colored flowers with fewer petaloids.

Plants of the new *Hibiscus* can be compared to plants of the *Hibiscus syriacus* 'Notwood3', disclosed in U.S. Plant Pat. No. 20,574. In side-by-side comparisons conducted in Grand Haven, Mich., plants of the new *Hibiscus* differed from plants of 'Notwood3' primarily in flower color as plants of 'Notwood3' had blue-colored flowers. In addition, plants of the new *Hibiscus* were not as vigorous as plants of 'Notwood3'.

Plants of the new *Hibiscus* can also be compared to plants of the *Hibiscus syriacus* 'Notwoodtwo', disclosed in U.S. Plant Pat. No. 12,612. In side-by-side comparisons conducted in Grand Haven, Mich., plants of the new *Hibiscus* differed from plants of 'Notwoodtwo' primarily in flower color as plants of 'Notwoodtwo' had white-colored flowers. In addition, plants of the new *Hibiscus* were not as vigorous as plants of 'Notwoodtwo'.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet is a side perspective view of a typical plant of 'JWNWOOD 4' grown in a ground bed in an outdoor nursery.

The photograph on the second sheet is a close-up view of typical flowering plant of 'JWNWOOD 4'.

DETAILED BOTANICAL DESCRIPTION

The aforementioned photographs and following observations, measurements and values describe plants grown in Grand Haven, Mich. during the summer in a ground bed in an outdoor nursery and under cultural conditions which closely approximate commercial *Hibiscus* production. Plants were three years old when the photographs and the description were taken. In the following detailed description, color references are made to The Royal Horticultural Society Colour Chart, 1995 Edition, except where general terms of ordinary dictionary significance are used.

Botanical classification: *Hibiscus syriacus* 'JWNWOOD 4'.

Parentage:

*Female, or seed, parent*.—Proprietary selection of *Hibiscus syriacus* identified as code number 3311, not patented.

*Male, or pollen, parent*.—Proprietary selection of *Hibiscus syriacus* identified as code number 4243, not patented.

Propagation:

*Type*.—By softwood cuttings.

*Time to initiate roots*.—About 45 days at 20° C.

*Time to produce a rooted young plant*.—About four months at 20° C.

*Root description*.—Thick to fine, fibrous.

*Rooting habit*.—Freely branching.

Plant description:

*Plant form and growth habit*.—Perennial deciduous shrub; upright and outwardly spreading plant habit; moderately vigorous growth habit.

*Branching habit*.—Freely branching habit, usually about 32 lateral branches develop per plant; pinching enhances lateral branch development.

*Plant height*.—About 1.5 meters.

*Plant diameter* (*area of spread*).—About 1 meter.

Lateral branch description:

*Length*.—About 42 cm.

*Diameter*.—About 4 mm.

*Internode length*.—About 3.8 cm.

*Texture, immature*.—Smooth, glabrous.

*Texture, mature*.—Woody.

*Color, immature*.—Close to 137A.

*Color, mature*.—Close to 198A.

Foliage description:

*Arrangement*.—Alternate, simple.

*Length*.—About 10 cm.

*Width*.—About 5 cm.

*Shape*.—Ovate to rhomboid.

*Apex*.—Narrowly acute.

*Base*.—Cuneate.

*Margin*.—Crenate; lobed.

*Texture, upper and lower surfaces*.—Smooth, glabrous.

*Venation pattern*.—Palmate; reticulate.

*Color*.—Developing leaves, upper surface: Close to 146B. Developing leaves, lower surface: Close to 146C. Fully expanded leaves, upper surface: Close to 147A; venation, close to 146B. Fully expanded leaves, lower surface: Close to 147B; venation, close to 146C.

*Petiole*.—Length: About 1.5 cm. Diameter: About 1.5 mm. Texture, upper and lower surfaces: Smooth, glabrous. Color, upper and lower surfaces: Close to 146B.

Flower description:

*Flower appearance and arrangement*.—Single rotate flowers; flowers terminal and axillary; freely flowering habit with usually about eight flowers per lateral branch; flowers face upright to outwardly.

*Flower longevity*.—Flowers last for about one day on the plant; flowers not persistent.

*Natural flowering season*.—Plants of the new *Hibiscus* flower from July 1 through September 15 in Michigan.

*Flower diameter*.—About 10 cm.

*Flower length* (*height*).—About 6 cm.

*Flower buds*.—Length: About 2 cm. Diameter: About 1.5 cm. Shape: Ovate. Color: Close to 147C.

*Petals*.—Arrangement and quantity: Single whorl of five petals; petals imbricate. Length: About 5.5 cm. Width: About 5 cm. Shape: Obovate. Apex: Broadly obtuse. Base: Attenuate. Margin: Entire; undulate. Texture, upper and lower surfaces: Smooth, glabrous. Color: When opening, upper surface: Close to 48A. When opening, lower surface: Close to 48C. Fully opened, upper surface: Close to 68D and 69A; towards the base and venation, close to 59A. Fully opened, lower surface: Close to 68D and 69A.

*Petaloids*.—Arrangement and quantity: About 22 petaloids in several whorls; petaloids imbricate. Length: About 3 cm. Width: About 1 cm. Shape: Roughly spatulate. Apex: Obtuse. Base: Attenuate. Margin: Entire; undulate. Texture, upper and lower surfaces: Smooth, glabrous. Color, upper and lower surfaces: Close to 68D.

*Sepals*.—Arrangement and quantity: Single whorl of five sepals fused into a tubular calyx. Length: About 1.2 cm. Width: About 9 mm. Shape: Roughly ovate. Apex: Acute to acuminate. Margin: Entire. Texture, upper and lower surfaces: Smooth, glabrous. Color, immature and mature, upper and lower surfaces: Close to 146B.

*Peduncles*.—Length: About 1.5 cm. Diameter: About 2 mm. Strength: Strong. Texture: Smooth, glabrous. Angle: Erect to about 30° from the stem. Color: Close to 146B.

*Reproductive organs*.—Androecium: Anther shape: Globular. Anther size: About 1 mm by 1 mm. Anther color: Close to 155B. Amount of pollen: Moderate. Pollen color: Close to 162A. Gynoecium: Style length: About 3 cm. Style color: Close to 155A.

Stigma appearance: Five-parted, rounded. Stigma color: Close to 155C. Ovary color: Close to 157A. Seeds: Quantity per flower: Up to five. Length: About 2.5 mm. Diameter: About 2.5 mm. Color: Close to 187A.

Garden performance: Plants of the new *Hibiscus* have been observed to have excellent garden performance and to tolerate rain, wind and temperatures ranging from about −10° C. to about 35° C.

Pathogen & pest resistance: Plants of the new *Hibiscus* have not been shown to be resistant to pathogens and pests common to *Hibiscus* plants.

It is claimed:

1. A new and distinct *Hibiscus* plant named 'JWNWOOD 4' as illustrated and described.

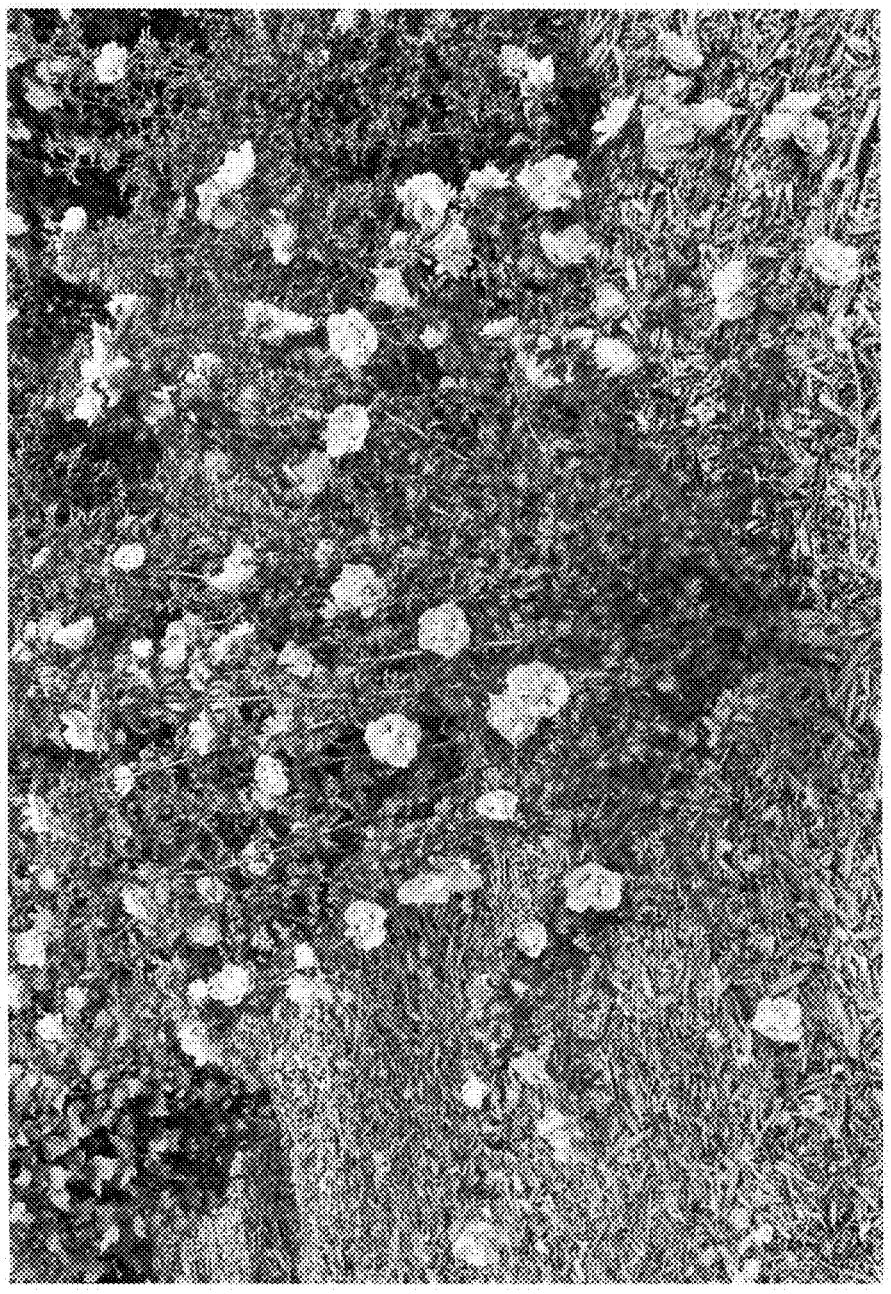

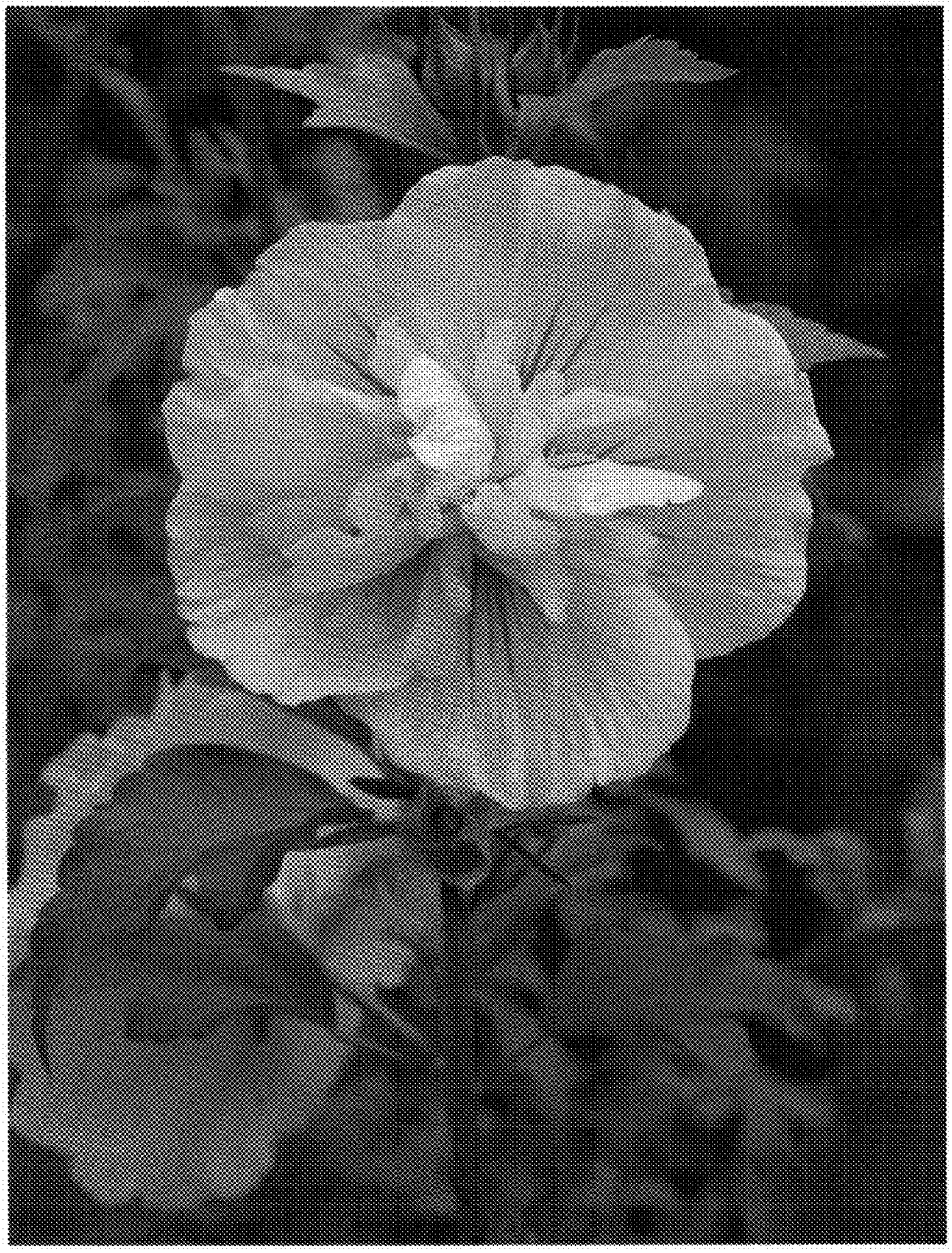

* * * * *